(12) United States Patent
Madden et al.

(10) Patent No.: US 12,403,237 B2
(45) Date of Patent: Sep. 2, 2025

(54) AUTOMATIC INFUSION VALVE

(71) Applicant: Alcon Inc., Fribourg (CH)

(72) Inventors: Sean Christopher Madden, Mission Viejo, CA (US); Parthasarathy Parishram, Irvine, CA (US)

(73) Assignee: Alcon Inc, Fribourg (CH)

(*) Notice: Subject to any disclaimer, the term of this patent is extended or adjusted under 35 U.S.C. 154(b) by 865 days.

(21) Appl. No.: 17/644,220

(22) Filed: Dec. 14, 2021

(65) Prior Publication Data
US 2022/0193323 A1 Jun. 23, 2022

Related U.S. Application Data

(60) Provisional application No. 63/126,675, filed on Dec. 17, 2020.

(51) Int. Cl.
*A61M 1/00* (2006.01)
*A61F 9/007* (2006.01)

(52) U.S. Cl.
CPC ......... *A61M 1/774* (2021.05); *A61F 9/00754* (2013.01); *A61M 1/742* (2021.05); *A61M 1/743* (2021.05); *A61M 2210/0612* (2013.01)

(58) Field of Classification Search
CPC ...... A61M 1/774; A61M 1/742; A61M 1/743; A61M 2210/0612; A61M 3/0283; A61M 1/772; A61M 2205/7536; A61M 1/85; A61M 1/77; A61M 3/0233; A61M 1/74; A61M 39/223; A61F 9/00754; A61F 9/00736
See application file for complete search history.

(56) References Cited

U.S. PATENT DOCUMENTS

| 3,851,650 A | 12/1974 | Darling |
| 4,030,495 A | 6/1977 | Virag |

(Continued)

FOREIGN PATENT DOCUMENTS

| EP | 0596314 A2 | 5/1994 |
| WO | 2021067316 A1 | 4/2021 |

OTHER PUBLICATIONS

U.S. Appl. No. 63/594,866, filed Oct. 31, 2023 (claiming priority to U.S. Appl. No. 63/594,866, filed Oct. 31, 2023).
(Continued)

*Primary Examiner* — Yashita Sharma
*Assistant Examiner* — Lei Gonzalez

(57) ABSTRACT

The present disclosure generally relates to fluid control valves for delivering and/or aspirating fluid during ophthalmic surgeries and procedures. In one embodiment, a valve assembly includes a first portion configured to fluidly couple with a gas supply line and a second portion configured to fluidly couple with a liquid supply line and an infusion line. The first portion and the second portion are partitioned or separated from each other by a filter having a hydrophobic membrane configured to prevent the flow of liquids therethrough while allowing the free flow of gas. Accordingly, an infusion liquid may be flown through the second portion while gases may be simultaneously aspirated through the first portion, without any liquids travelling into the gas supply line. The gas supply line may thus be utilized to vent or purge gases from the infusion line before or during performance of surgical procedures.

15 Claims, 10 Drawing Sheets

(56) References Cited

U.S. PATENT DOCUMENTS

| | | | |
|---|---|---|---|
| 4,558,708 A | 12/1985 | Labuda et al. | |
| 4,722,366 A | 2/1988 | Maaskamp | |
| 4,758,238 A | 7/1988 | Sundblom et al. | |
| 4,813,927 A | 3/1989 | Morris | |
| 5,935,100 A | 8/1999 | Myers | |
| 7,238,224 B2 * | 7/2007 | Kent | B01D 63/089 347/92 |
| 7,713,237 B2 | 5/2010 | Nazarifar et al. | |
| 7,717,129 B2 * | 5/2010 | Steppe | F16K 15/147 137/846 |
| 8,746,290 B2 | 6/2014 | Hopkins | |
| 8,801,684 B2 | 8/2014 | Walti et al. | |
| 9,132,229 B2 | 9/2015 | Gao et al. | |
| 9,308,738 B2 * | 4/2016 | Arima | B41J 2/18 |
| 9,505,505 B2 | 11/2016 | Hopkins | |
| 10,434,010 B2 | 10/2019 | Auld | |
| 2005/0077225 A1 | 4/2005 | Usher et al. | |
| 2006/0090645 A1 | 5/2006 | Kent | |
| 2008/0066816 A1 | 3/2008 | Steppe et al. | |
| 2008/0103432 A1 | 5/2008 | Sanchez | |
| 2016/0367745 A1 * | 12/2016 | Liu | A61M 1/1672 |
| 2017/0273826 A1 | 9/2017 | Sanchez, Jr. | |
| 2018/0104391 A1 * | 4/2018 | Luxon | A61M 1/73 |
| 2018/0200750 A1 * | 7/2018 | Ramina | B05C 21/00 |
| 2021/0402086 A1 | 12/2021 | Jokaji et al. | |

OTHER PUBLICATIONS https://www.bvimedical.com/ophthalmic-products/automatic-bss-air-infusion-control-system/ accessed on Aug. 21, 2020, 2 pages.
https://www.qosina.com/transducer-protectors, accessed on Jul. 28, 2020, 3 pages.
https://www.sterlitech.com/hydrophobic-polycarbonate-membrane-filter-pctf10025100.html, accessed on Aug. 6, 2020, 15 pages.
https://www.sterlitech.com/hydrophobic-polycarbonate-membrane-filter-pctf8013100.html, accessed on Aug. 6, 2020, 13 pages.
Polycarbonate Track Etch (PCTE) Membrane Filters, Datasheet 1, Sterlitech Catalog 2016, accessed on Aug. 6, 2020, 1 page.
Polycarbonate Track Etch (PCTE) Membrane Filters, Datasheet 2, Sterlitech Catalog 2016, accessed on Aug. 6, 2020, 1 page.

* cited by examiner

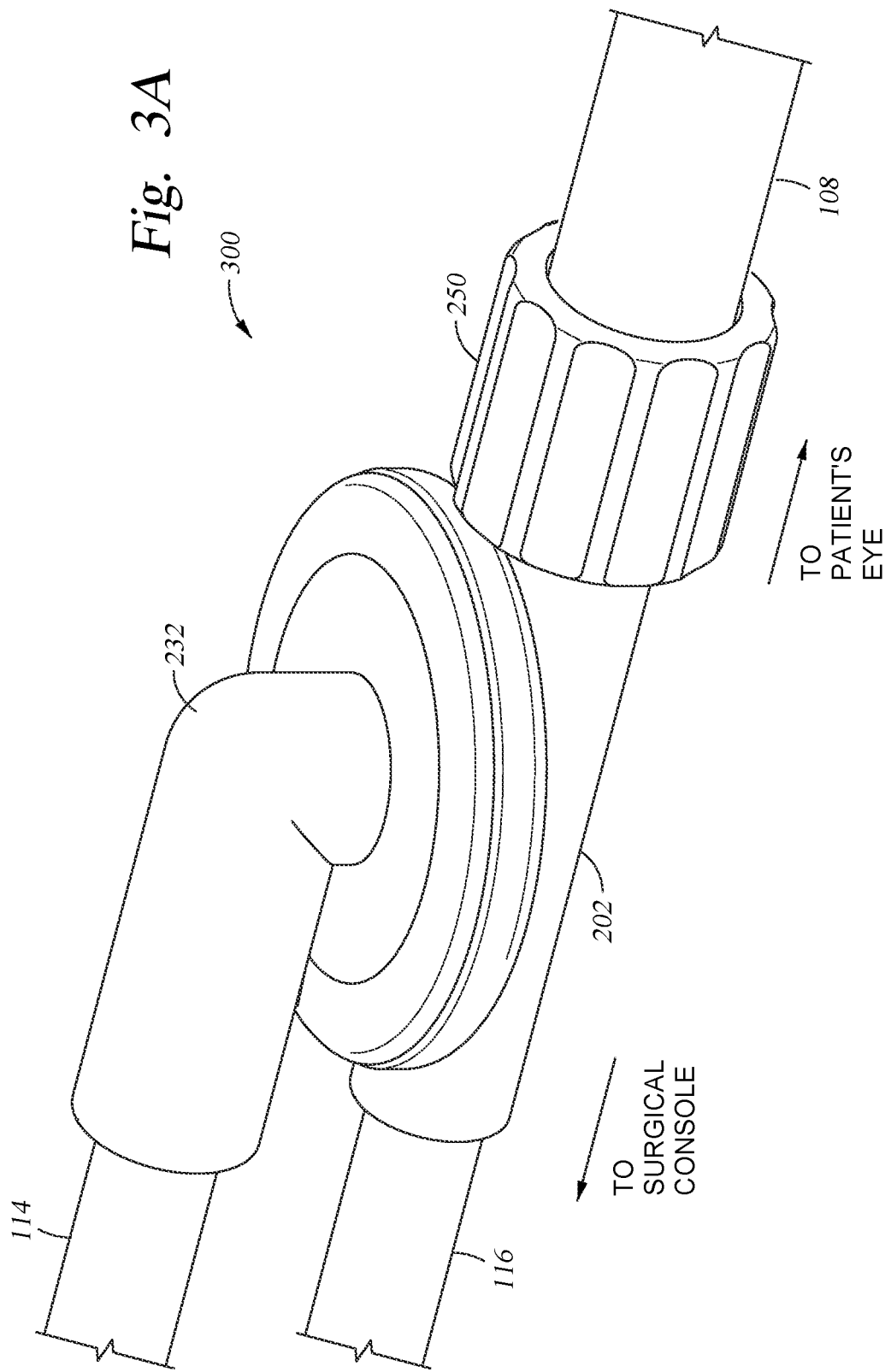

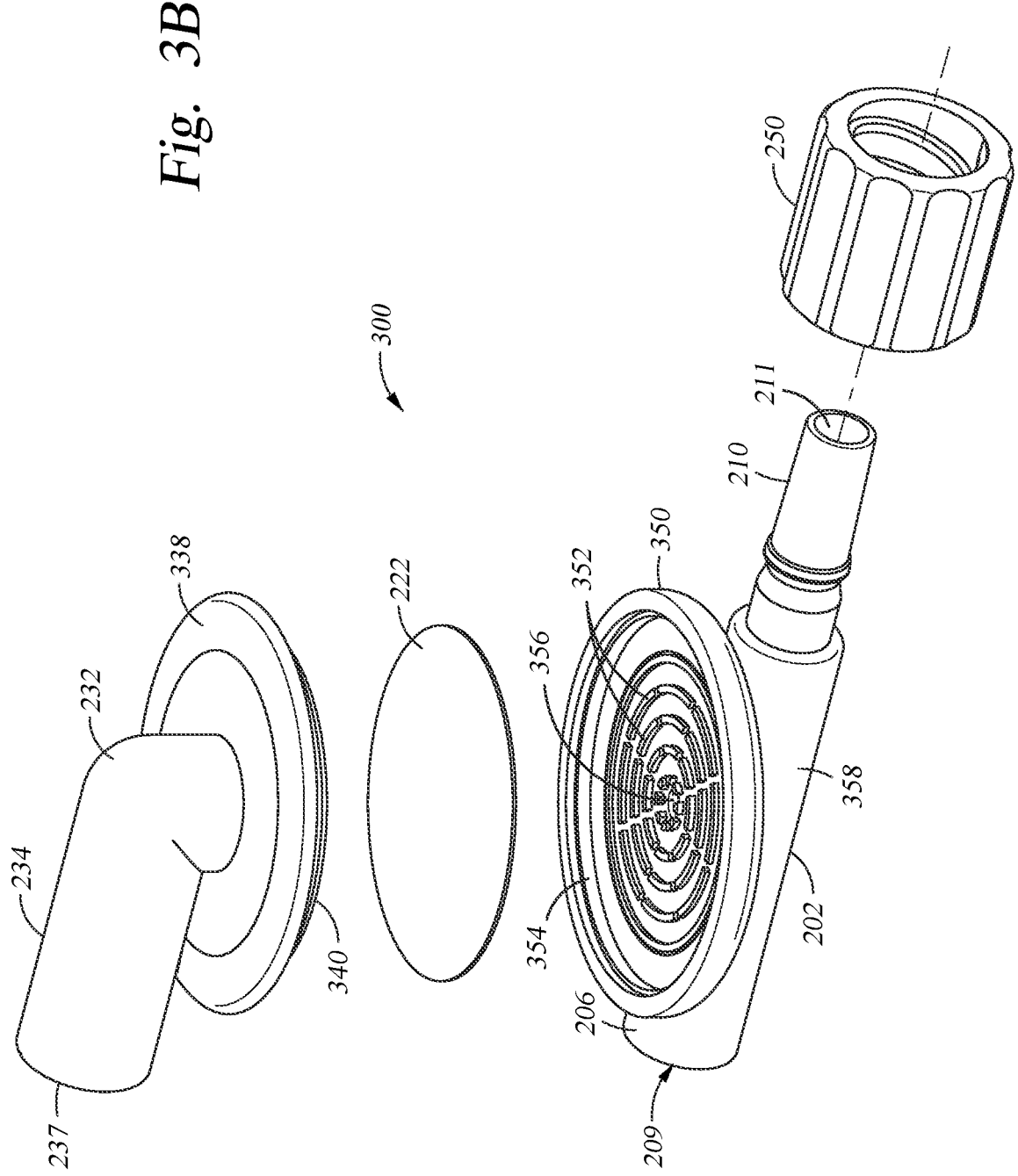

AUTOMATIC INFUSION VALVE

PRIORITY CLAIM

This application claims the benefit of priority of U.S. Provisional Patent Application Ser. No. 63/126,675 titled "AUTOMATIC INFUSION VALVE," filed on Dec. 17, 2020, whose inventors are Sean Christopher Madden and Parthasarathy Parishram, which is hereby incorporated by reference in its entirety as though fully and completely set forth herein.

BACKGROUND

Field

Embodiments of the present disclosure generally relate to devices for ophthalmic procedures, and more particularly, to devices for intraocular fluid delivery.

Description of the Related Art

Microsurgical procedures frequently require precision cutting, removal, and manipulation of various body tissues. For example, certain ophthalmic surgical procedures, such as pars plana vitrectomies, require cutting and removal of portions of the vitreous humor, a transparent gel-like material that fills the posterior segment of the eye. Simultaneously while removing the vitreous humor, a liquid solution (e.g., balanced salt solution (BSS)) is typically infused into the eye to maintain intraocular pressure and prevent collapse of the eye wall. In cases of retinal breaks or retinal detachment, the liquid solution may then be exchanged for air, through a process known as fluid-air exchange, to help push out subretinal fluid from the intraocular space while maintaining intraocular pressure and temporarily holding the retina in place. During such procedures, the liquid and air are provided by separate supply lines that are conjoined with a singular downstream infusion line via a stopcock.

In some cases, the air pressure in the gas supply line may build up and cause air to escape into the infusion line, forming air bubbles in the infusion liquid which may travel to the eye and negatively affect intraocular pressure during surgery. Conventional designs for check valves of infusion stopcocks, however, do not allow venting through the gas supply line without reverse leakage of liquid and thus, there is currently no effective way to remove the air bubbles or prevent their escape into infusion liquids. Additionally, during some procedures, infusion fluids must be back-flowed through the infusion line in order for other surgical fluids, such as a retinal tamponade, to be injected into the intraocular space. In such cases, the amount of infusion fluid that may be back-flowed is limited by the inability to purge infusion gases through the gas supply line without reverse leakage of liquids therein, which may damage the air pump and/or cause additional complications during fluid infusion.

Therefore, what is needed in the art are improved fluid control valves for ophthalmic fluid infusion that enable aspiration and purging of gases.

SUMMARY

The present disclosure generally relates to devices for surgical procedures, and more particularly, surgical devices for ophthalmic fluid infusion and aspiration.

In certain embodiments, a valve assembly for fluid infusion is provided. The valve assembly includes a first portion with a first conduit having a first port and a first cavity having a proximal end and a distal end opposite of the proximal end. The proximal end is fluidly coupled to the first port via the first conduit, and the distal end has a cross-sectional area greater than a cross-sectional area of the first conduit. The valve assembly further includes a second portion with a second conduit having a second port, a third conduit having a third port, and a second cavity disposed between the second conduit and the third conduit and fluidly coupling the second port to the third port, where the second cavity is adjacent to the first cavity. A filter having a hydrophobic membrane is disposed between and partitions the first cavity from the second cavity and the hydrophobic membrane partially defines the second cavity.

In certain embodiments, a fluid infusion system for ophthalmic procedures is provided. The fluid infusion system includes a surgical console having a first fluid line coupled to a gas fluid source and a second fluid line coupled to a liquid fluid source. The fluid infusion system further includes a valve assembly fluidly coupled to the first fluid line and the second fluid line. The valve assembly includes a first conduit having a first port in fluid communication with the first fluid line, a second conduit having a second port in fluid communication with the second fluid line, and a third conduit having a third port in fluid communication with a third fluid line. Flow rates of fluids through the first, second, and third lines is controlled by the surgical console The first, second, and third conduits are further coupled to an intermediary cavity and in fluid communication with each other. A filter is disposed within the intermediary cavity and partitions the first conduit from the second and third conduits. The filter includes a hydrophobic membrane disposed on a side thereof opposite the first conduit and configured to prevent flow of liquids from the second and third conduits into the first conduit while allowing bi-directional flow of gases therebetween.

BRIEF DESCRIPTION OF THE DRAWINGS

So that the manner in which the above-recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 3A illustrates a perspective view of an exemplary valve assembly, according to certain embodiments of the present disclosure.

FIG. 3B illustrates a perspective exploded view of the valve assembly of FIG. 3A, according to certain embodiments of the present disclosure.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

The present disclosure generally relates to fluid control valves for delivering and/or aspirating fluid during ophthalmic surgeries and procedures. For example, the fluid control valves described herein may be used during vitrectomies, such as pars plana vitrectomies for the treatment of posterior segment diseases. Vitrectomies typically require cutting and removal of portions of the vitreous humor. In order to maintain intraocular pressure and prevent collapse of the eye during such surgical procedures, liquid is infused into the intraocular space and thereafter aspirated. In certain procedures, the liquid is then exchanged with air or other gases during a process known as fluid-air exchange. During such processes, it is typically beneficial to purge or vent any undesired gases in the infusion line and/or the intraocular space to maintain intraocular pressure. The fluid control valves and methods described herein provide improved structures and mechanisms for infusion fluid flow regulation that enable upstream purging and/or venting of gases from infusion lines while also preventing liquids from the infusion lines to leak into the gas supply lines.

In certain embodiments, a valve assembly includes a first portion configured to fluidly couple with a gas supply line and a second portion configured to fluidly couple with a liquid supply line and an infusion line. The first portion and the second portion are partitioned or separated from each other by a filter having a hydrophobic membrane configured to prevent the flow of liquids therethrough while allowing the free flow of gas. Accordingly, an infusion liquid may be flowed through the second portion while gases may be simultaneously aspirated into the first portion, without any liquids travelling into the gas supply line. The gas supply line may thus be utilized to vent or purge gases from the infusion line before or during performance of surgical procedures.

Figure 1:
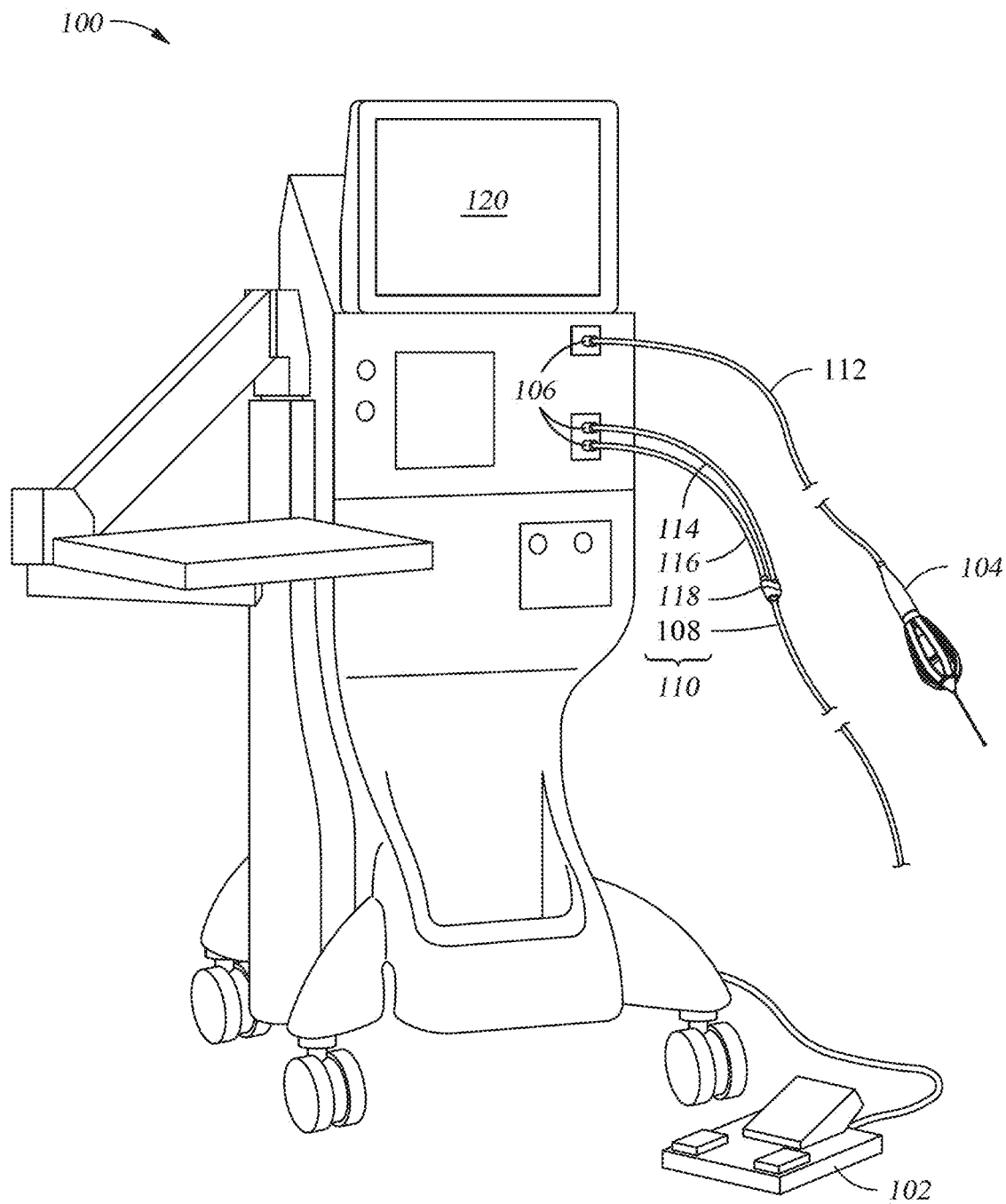
FIG. 1 illustrates a perspective view of an exemplary surgical console, according to certain embodiments of the present disclosure.

FIG. 1 illustrates a perspective view of an exemplary surgical console 100 that may be utilized in combination with the fluid control valves described herein. The surgical console 100 is operably coupled, physically or wirelessly, to any number of user interfaces, including a foot controller 102 and a surgical tool 104 such as a vitrector. The surgical console 100 provides one or more port connectors 106 for physically coupling the user interfaces to various components of the surgical console 100. For example, the surgical tool 104 may be fluidly coupled with a vacuum source via a vacuum supply line 112 disposed through a port connector 106 to enable aspiration of cut vitreous from the patient's eye. Similarly, one or more port connectors 106 may be utilized to couple a fluid infusion system 110 with one or more infusion fluid sources, (e.g., an air/gas source, a liquid perfluorocarbon source, a silicone oil infusion (SOI) source, a BSS source, etc.) to enable infusion of fluids into the eye during vitreous removal. As shown in FIG. 1, the fluid infusion system 110 includes an infusion line 108 fluidly coupled with a gas supply line 114 and a separate liquid supply line 116 at a three-way automatic valve assembly 118, which may enable selective flow of different infusion fluids through the infusion line 108.

In operation, the user may control an aspect or mechanism of the surgical tool 104 and/or the fluid infusion system 110 via actuation of the foot controller 102, which may include a foot pedal. For example, the user may press down on (e.g., depress) the foot controller 102 to initiate and increase a flow rate of an infusion fluid from a fluid source through the fluid infusion system 110 and into the eye of the patient. Alternatively, reducing depression of the foot controller 102 (e.g., lifting the user's foot) may decrease and ultimately stop the flow of fluid through the fluid infusion system 110. Accordingly, in certain embodiments, the flow rate of infusion fluids through the fluid infusion system 110 corresponds to the amount of depression of the foot controller 102. In certain embodiments, the surgical console 100 further includes a display 120 for displaying information to the user (the display may also incorporate a touchscreen for receiving user input). Thus, the display 120 may display information about infusion fluid parameters, such as infusion fluid flow rates and intraocular pressure, to the user during operation thereof.

Figure 2A:
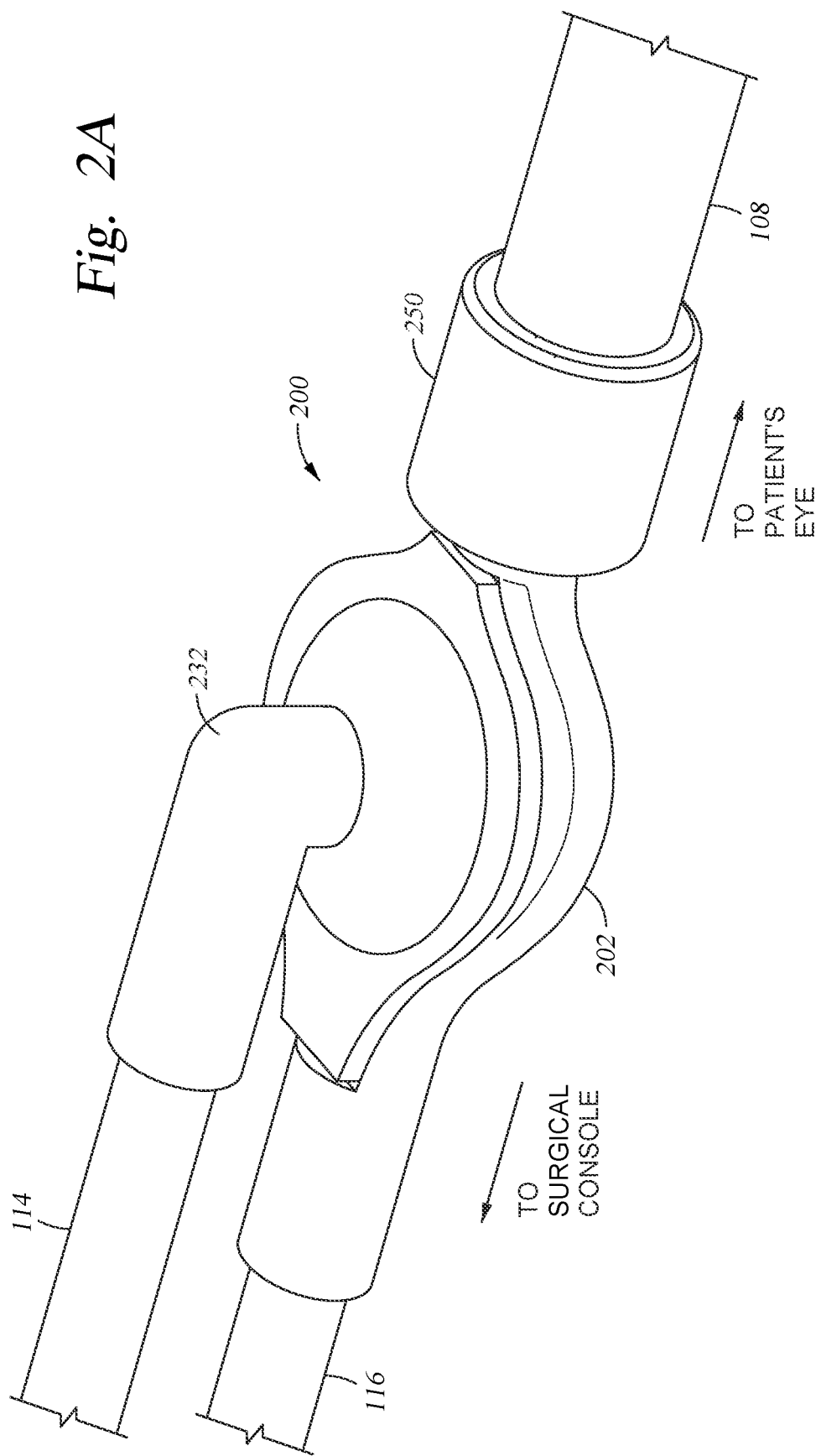
FIG. 2A illustrates a perspective view of an exemplary valve assembly, according to certain embodiments of the present disclosure.
Figure 2B:
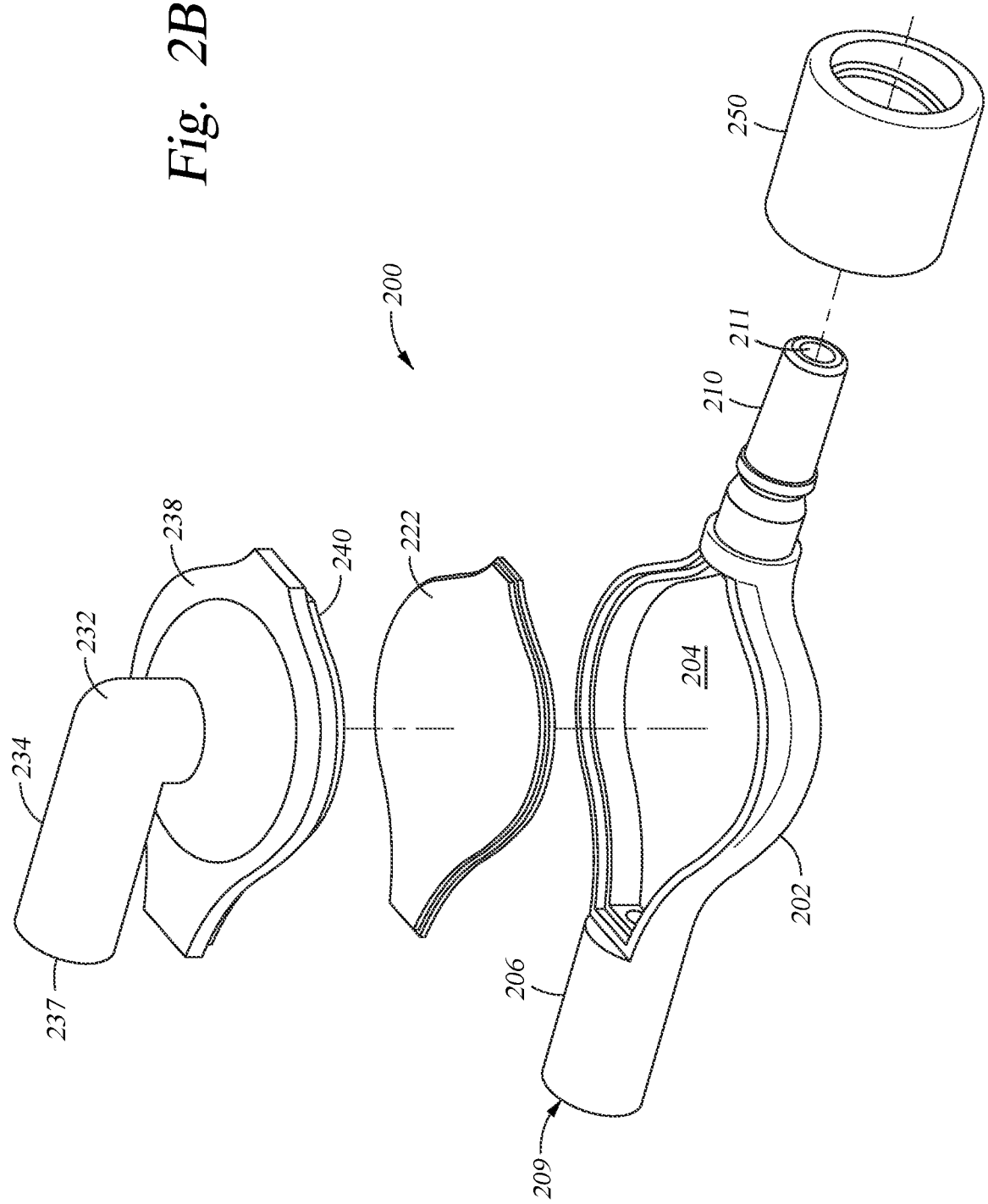
FIG. 2B illustrates a perspective exploded view of the valve assembly of FIG. 2A, according to certain embodiments of the present disclosure.
Figure 2C:
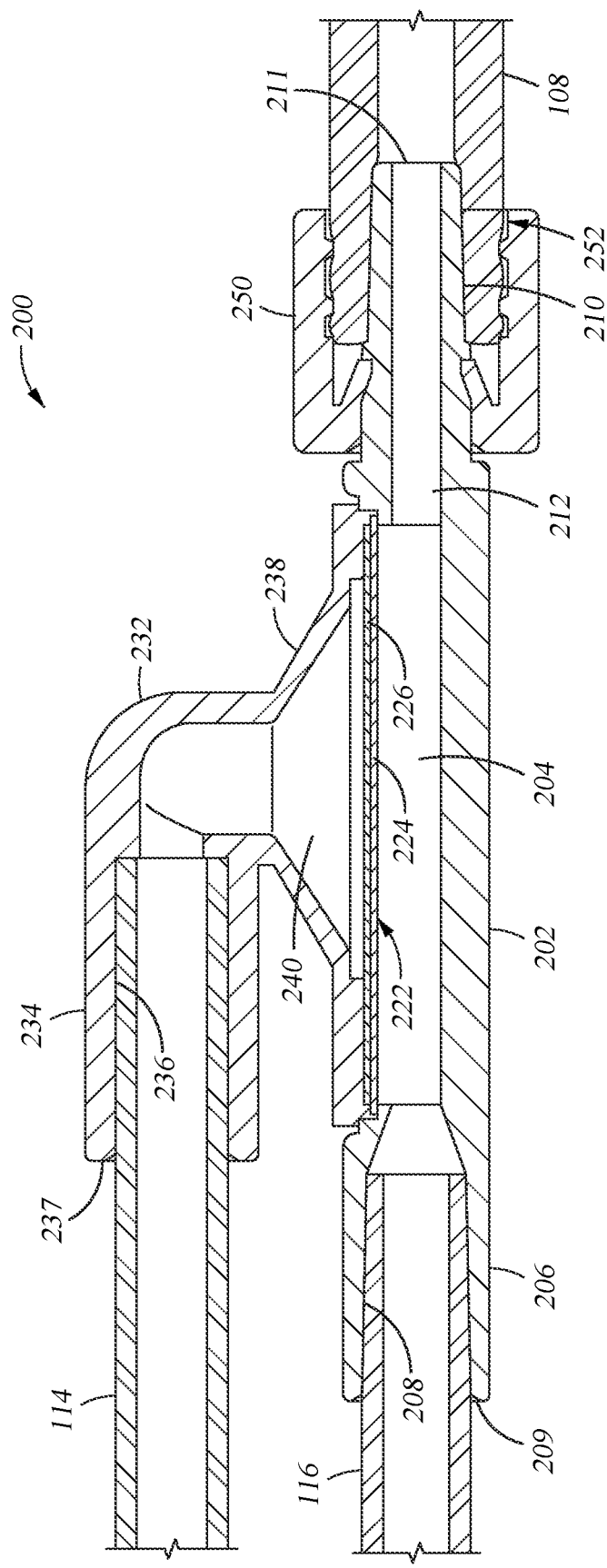
FIG. 2C illustrates a schematic cross-sectional view of the valve assembly of FIG. 2A, according to certain embodiments of the present disclosure.

FIGS. 2A-2C illustrate a valve assembly 200 for flow control of infusion fluids during surgical procedures. Valve assembly 200 is an example of the automatic three-way valve assembly 118, which may be utilized in combination with the fluid infusion system 110 and the surgical console 100 described above. As shown in more detail in FIGS. 2A-2C, the valve assembly 200 generally includes a hydrophobic filter (shown as hydrophobic filter 222 in FIGS. 2B-2C) disposed between valve assembly 200's first portion (e.g., an upper body), configured to fluidly couple with a gas supply line, and valve assembly 200's second portion (e.g., a lower body), configured to fluidly couple with a fluid supply line. The partitioning of the first portion and the second portion by the hydrophobic filter enables active bi-directional flow of gases, such as air, between the gas supply line and an infusion line while passively preventing liquids from travelling into the gas supply line. Thus, gases may be vented or purged from the fluid infusion system 110 during fluid infusion to enable improved control of intraocular pressure during surgical procedures.

FIG. 2A illustrates a perspective view of the valve assembly 200, while FIG. 2B illustrates a perspective exploded view thereof and FIG. 2C illustrates a cross-sectional view thereof. Accordingly, FIGS. 2A-2C are herein described together for clarity.

As noted above, the valve assembly 200 generally includes an upper body 232 configured to interface (e.g., couple) with a lower body 202. In certain embodiments, the upper body 232 and lower body 202 are formed of any suitable plastic materials, such as acrylonitrile butadiene styrene (ABS), polycarbonate (PC), nylon, and acrylic, which may be transparent or opaque in color. The upper body 232 has a base 238 from which an arm 234 extends in a proximal direction (e.g., toward a surgical console or gas source) for coupling with gas supply line 114. Note that, as described herein, a distal end or portion of a component refers to the end or portion that is closer in line to a patient's body during use thereof. On the other hand, a proximal end or portion of the component refers to the end or the portion that is distanced further away in line from the patient's body (e.g., closer to the surgical console).

The gas supply line 114 couples with a port 237 at a proximal end of the arm 234, which provides fluid connection with a conduit 236 extending through a length of the arm 234. In certain embodiments, a diameter of the port 237 is substantially the same or slightly larger than an outer diameter of the gas supply line 114 to allow a distal end of the gas supply line 114 to be securely fit within the port 237. In certain embodiments, the outer diameter of the proximal end of the arm 234 is substantially the same or slightly smaller than an inner diameter of the gas supply line 114 to allow the distal end of the gas supply line 114 to secure fit over the proximal end of the arm 234.

The conduit 236 extends from the proximal end of the arm 234 to a distal end of the arm 234 and opens into a cavity 240 within the base 238 of the upper body 232. In certain embodiments, the arm 234 and thus the conduit 236 have one or more curved portions to create an angled flow path for gases between the gas supply line 114 and the cavity 240. For example, the arm 234 and the conduit 236 may have a bend disposed at about a 90-degree angle between the proximal and distal ends thereof, thus creating an elbow-like gas flow path. The bending of the gas flow path enables a three-way connection of the valve assembly 200 between the gas supply line 114, the liquid supply line 116, and an infusion line 108.

The cavity 240 is disposed at the distal end of conduit 236 and generally has one or more dimensions greater than a width or diameter of the conduit 236. In certain embodiments, the cavity 240 has a cross-sectional area that gradually increases from an end of the cavity 240 nearest the arm 234 to an end of the cavity 240 furthest from the arm 234 (e.g., nearest the lower body 202). For example, the end of the cavity 240 nearest the arm 234 may have substantially the same cross-sectional area as the distal end of the conduit 236 while the end of the cavity 240 furthest from the arm 234 may have a cross-sectional area greater than a cross-sectional area of the distal end of the conduit 236. In certain embodiments, the cavity 240 has a frustoconical-like shape. The increased cross-sectional area of the cavity 240 at the distal end thereof enables utilization of a larger-area filter 222 between the upper body 232 and the lower body 202 and provides more surface area through which gases may be vented or purged from liquids flowing between the liquid supply line 116 and the infusion line 108.

Generally, a lower surface of the upper body 232 and an upper surface of the lower body 202 are configured to interface with or engage each other and secure the filter 222 therebetween. In certain embodiments, the lower body 202 couples to the upper body 232 at a lower surface of the base 238 such that the cavity 240 faces a chamber 204 (e.g., a second cavity or reservoir) located at a central position of the lower body 202. The chamber 204 may have a cross-sectional area substantially the same or greater than the cross-sectional area of the end of the cavity 240 nearest chamber 204 so as not to constrict air flow between the upper body 232 and the lower body 202 and vice versa. The lower body 202 further includes extensions 206 and 210 on opposing sides of the chamber 204, where each extension 206 and 210 has a conduit 208 or 212 formed therethrough, respectively. The conduits 208 and 212 extend from the chamber 204 in opposing directions toward ports 209 and 211 located at the proximal and distal ends of the extensions 206 and 210, respectively. In certain embodiments, the port 209 is configured to fluidly couple with a liquid supply line 116, while the port 211 is configured to couple to infusion line 108.

Similar to the port 237, the port 209 may have a diameter substantially the same or slightly larger than an outer diameter of the liquid supply line 116 to allow a distal end of the liquid supply line 116 to be securely fit within the port 209. Alternatively, an outer diameter of the proximal end of the extension 206 may be substantially the same or slightly smaller than an inner diameter of the liquid supply line 116 to allow the distal end of the liquid supply line 116 to securely fit over the proximal end of the extension 206. The extension 212, however, is generally sized to have an outer diameter substantially the same or slightly smaller than an inner diameter of the proximal end of the infusion line 108. Accordingly, the infusion line 108 is configured to securely fit around the extension 212. In certain embodiments, the extension 212 may include a locking mechanism, such as a Luer lock 250, which is configured to couple with the infusion line 108 and provide additional mechanical holding force for a leak-free seal between the valve assembly 200 and the infusion line 108. For example, the Luer lock 250 may comprise a threaded interior surface 252 through which the proximal end of the infusion line 108 may be secured within.

The filter 222 is disposed between the cavity 240 of the upper body 232 and the chamber 204 of the lower body 202, thus partially defining both the cavity 240 and the chamber 204. The filter 222 includes any suitable type of membrane filter having a hydrophobic membrane 224 permeable to gas. The hydrophobic membrane 224 may also be capable of capturing individual viruses and bacteria, thus acting as a sterile barrier to prevent viruses and bacteria from entering the eye from the low pressure gas source.

In some examples, the filter 222 includes a membrane 224 formed of polytetrafluoroethylene (PTFE), expanded PTFE (ePTFE), polycarbonate track etch (PCTE), polyesters (e.g., polyethylene terephthalate (PET)), nylon, cellulose (e.g., surfactant free cellulose acetate (SCFA), cellulose nitrate (CN), cellulose acetate (CA), polyethersulfone (PES), glass fibers, or acrylic copolymers. The membrane 224 may further be unsupported or supported by a backing 226 formed of materials including but not limited to polyester, polyethylene, polypropylene, or nylon. For example, in certain embodiments, the filter 222 includes an ePTFE membrane 224 having a polyester backing 226. Generally, the hydrophobic membrane 224 of the filter 222 is oriented to face the chamber 204 so as to prevent liquids from flowing from the chamber 204 through the filter 222 and into the cavity 240. The membrane 224 has a pore size ranging between about 0.1 μm to about 10.0 μm, such as between about 0.2 μm to about 5 μm, such as between about 0.5 μm to about 3.0 μm, such as a between about 0.8 μm to about 1.2 μm. Furthermore, the membrane 224 may have a thickness ranging between about 150 μm to about 300 μm, such as between about 200 μm to about 250 μm.

During operation, infusion liquid from the liquid source, such as silicone oil or balanced salt solution (BSS), may flow through the liquid supply line 116, into the lower body 202 of the valve assembly 200, and through the infusion line 108 toward the patient's eye and vice-versa. Alternatively, infusion gases from the gas source, such as air, may flow through the gas supply line 114, into the upper body 232, past the filter 222 into the lower body 202, and then into the infusion line 108 toward the patient's eye and vice-versa. The placement of the hydrophobic filter 222 between the upper body 232 and the lower body 202 passively prevents liquid from flowing up into the upper body 232 and the gas supply line 114, while allowing gases to pass therethrough. Accordingly, the valve assembly 200 enables the venting, purging, and/or back-flow of gases during fluid infusion procedures while preventing the escape of liquid into the gas supply line 116, which is described in further detail below.

Please note that although a single filter 222 is depicted in FIGS. 2A-2C, in certain embodiments, it is further contemplated that the valve assembly 200 may include two or more filters arranged in a linear or stacked configuration. The two or more filters may be formed of different materials and/or have different pore sizes relative to each other. For example, in certain embodiments, the valve assembly 200 may include a second filter disposed between the upper and lower bodies 232, 202 and upstream of the filter 222 (e.g., closer in line to the gas supply line 114). In such embodiments, the second filter may have a pore size smaller than the filter 222 and provide filtration of gases flowed through the gas supply line 114, while the filter 222 provides a hydrophobic barrier to prevent leakage of liquid therein.

Figure 3C:
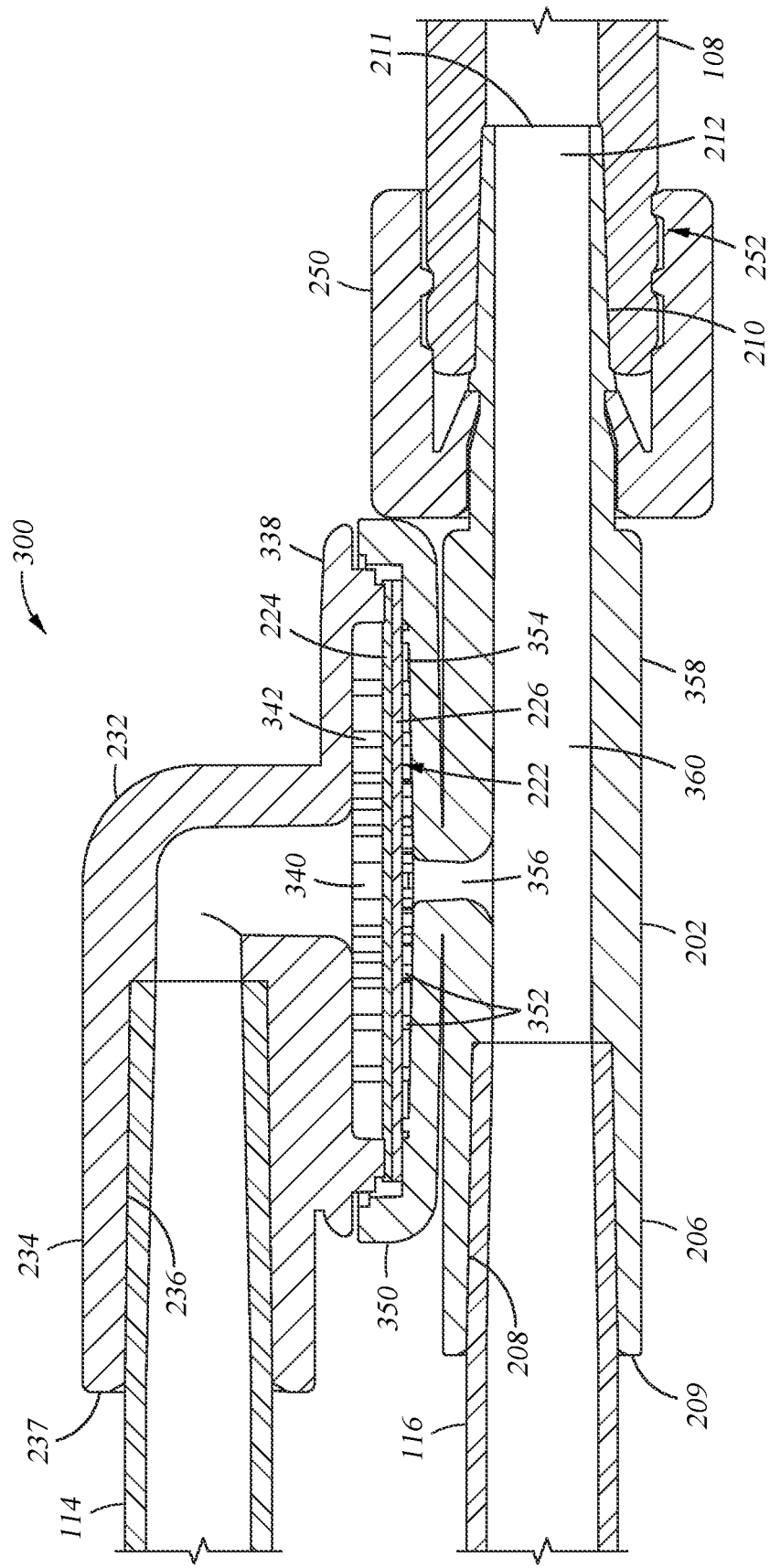
FIG. 3C illustrates a schematic cross-sectional view of the valve assembly of FIG. 3A, according to certain embodiments of the present disclosure.

FIGS. 3A-3C illustrate another valve assembly 300, which functions in substantially the same manner as the valve assembly 200 depicted in FIGS. 2A-2C, but with a different structure. Accordingly, FIGS. 3A-3C are described together for clarity, and parts of the valve assembly 300 corresponding to the above-described parts of the valve assembly 200 are marked with the same reference numerals.

As shown, the upper body 232 of the valve assembly 300 includes a base 338, which generally has a plate-like shape and further includes one or more ridges (e.g., ribs or grooves) 342 extending from a lower surface thereof that form one or more channels within a cavity 340 (shown in FIG. 3C). In certain embodiments, the ridges 342 are annular or semi-annular ridges that circumscribe the distal end of the conduit 236. The ridges 342 provide added support for the filter 222 when the valve assembly 300 is in an assembled state.

Similar to the cavity 240 of the valve assembly 200, the cavity 340 fluidly couples with the conduit 236 and has one or more cross-sectional dimensions greater than a width or diameter of the conduit 236. However, unlike the cavity 240, the cavity 340 has a cross-sectional area that steeply or abruptly increases from an end of the cavity 340 nearest the arm 234 to an end of the cavity 340 furthest from the arm 234. As described above, the increased cross-sectional area of the cavity 340 enables utilization of a larger-area filter 222, which provides more surface area through which gases may be vented or purged from liquids flowing between the liquid supply line 116 and the infusion line 108.

The lower body 202 of the valve assembly 300 includes a basin 350 coupled to a flow-through member 358. The basin 350 is configured to interface and engage with the base 338 of the upper body 232 and secure the filter 222 therebetween. In certain embodiments, the basin 350 couples to the upper body 232 at a lower surface of the base 338 such that the cavity 340 of the base 338 faces a cavity 354 of the basin 350. At least a portion of the cavity 354 may have a cross-sectional area substantially the same or greater than the cross-sectional area of the end of the cavity 340 nearest the basin 350 so as not to constrict air flow between the upper body 232 and the lower body 202 and vice versa. For example, an end of the cavity 354 opposite the flow-through member 358 may have a cross-sectional area substantially the same or greater than the cross-sectional area of the end of the cavity 340 nearest the basin 350.

Similar to the base 338, the basin 350 includes one or more ridges 352 extending from an upper surface thereof into a cavity 354. The ridges 352 are configured to provide support to the filter 222 when the valve assembly 300 is in an assembled state and may be annular or semi-annular in shape, defining one or more channels therein. In certain embodiments, the ridges 352 circumscribe a proximal end of a channel 356 that fluidly couples the cavity 354 with an intermediate conduit 360 of the flow-through member 358. The intermediate conduit 360, in turn, extends and fluidly connects the extensions 206 and 210 of the lower body 202, which are configured to couple with the liquid supply line 116 and the infusion line 108 at ports 209 and 211, respectively.

During operation of the valve assembly, infusion liquid from the liquid source may flow through the liquid supply line 116, into the flow-through member 358 of the lower body 202, and through the infusion line 108 toward the patient's eye and vice versa. Alternatively, infusion gases from the gas source may flow through the gas supply line 114, into the upper body 232, past the filter 222 into the lower body 202, and through the infusion line 108 toward the patient's eye and vice-versa. Similar to the valve assembly 200, the disposition of the hydrophobic filter 222 between the upper body 232 and the lower body 202 passively prevents the flow of liquids into the upper body 232 and the gas supply line 114, while allowing gases to pass therethrough. Thus, like the valve assembly 200, the valve assembly 300 facilitates venting, purging, and/or back-flow of gases during fluid infusion procedures while preventing the escape of liquid into the gas supply line 114.

Please note that, as discussed above with reference to the valve assembly 200, although a single filter 222 is depicted in FIGS. 3A-3C, it is further contemplated that the valve assembly 300 may include two or more filters arranged in a linear or stacked configuration. The two or more filters may be formed of different materials and/or have different pore sizes relative to each other. For example, in certain embodiments, a second filter having a finer pore size may be disposed upstream of the filter 222 to provide additional filtration of gases flowed through the gas supply line 114, while the filter 222 provides a hydrophobic barrier and prevent liquids from flowing therein.

Figure 4A:
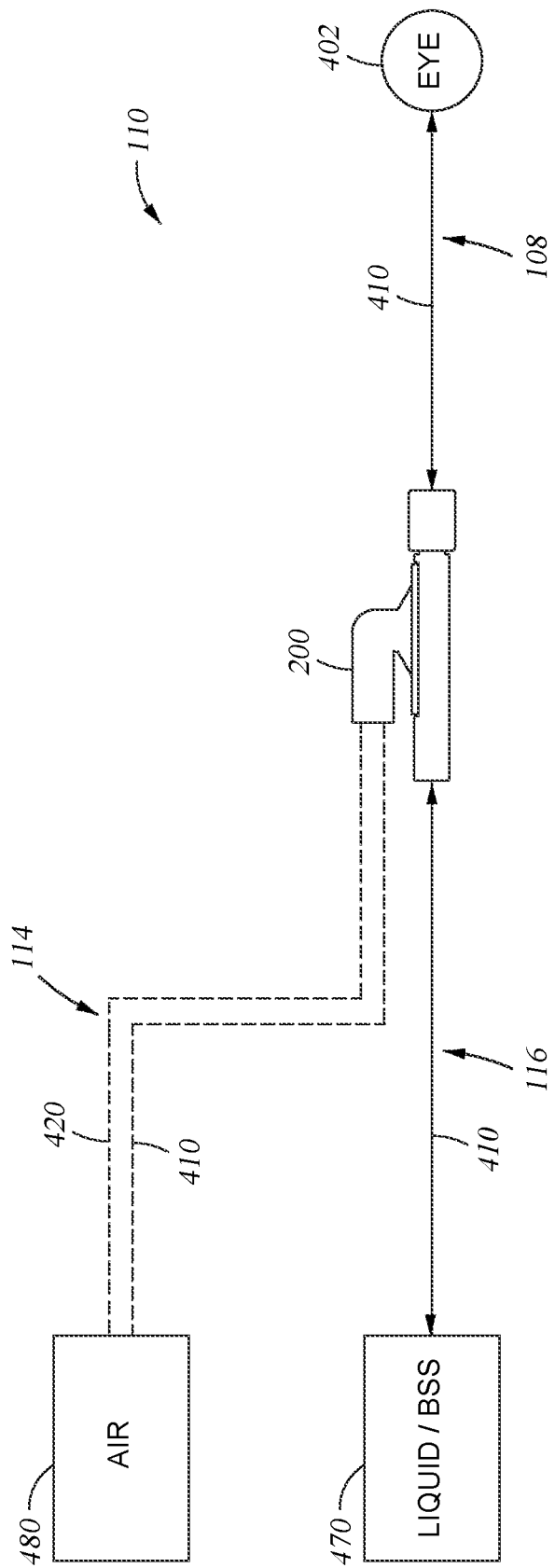
FIG. 4A illustrates a schematic plan view of an exemplary operational mode of the valve assemblies of FIGS. 2A-2C and 3A-3C, according to certain embodiments of the present disclosure.
Figure 4B:
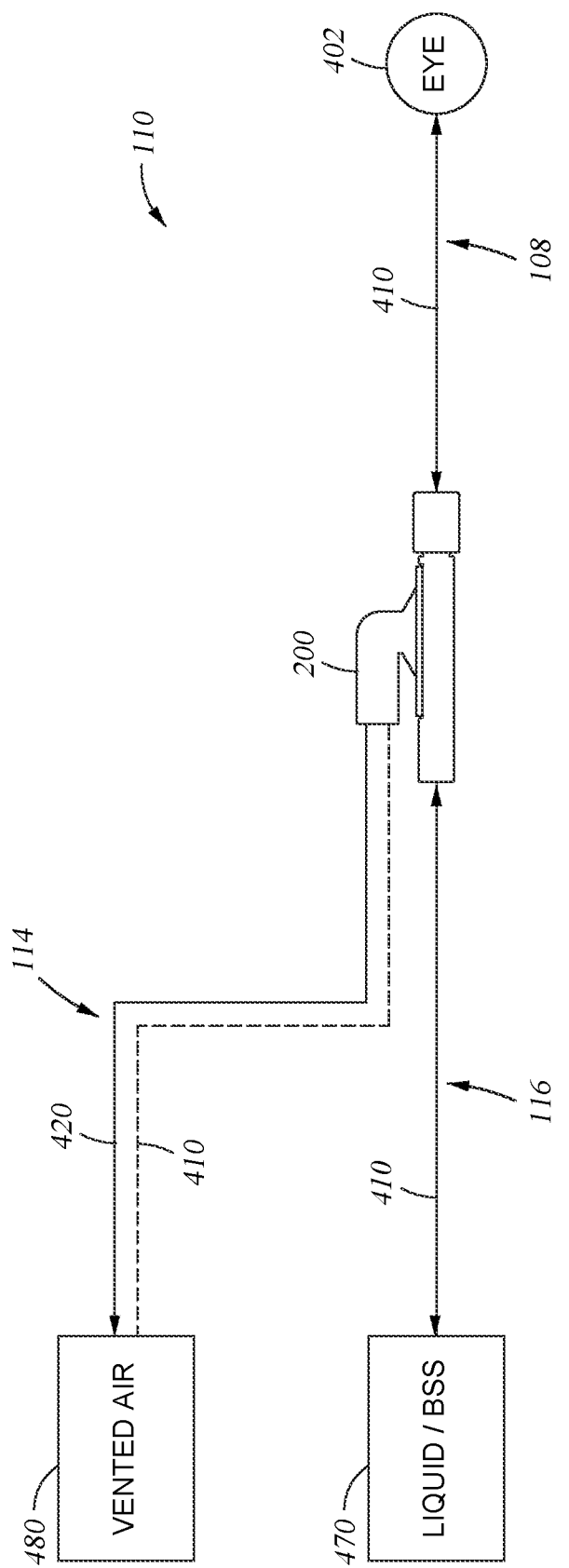
FIG. 4B illustrates a schematic plan view of an exemplary operational mode of the valve assemblies of FIGS. 2A-2C and 3A-3C, according to certain embodiments of the present disclosure.
Figure 4C:
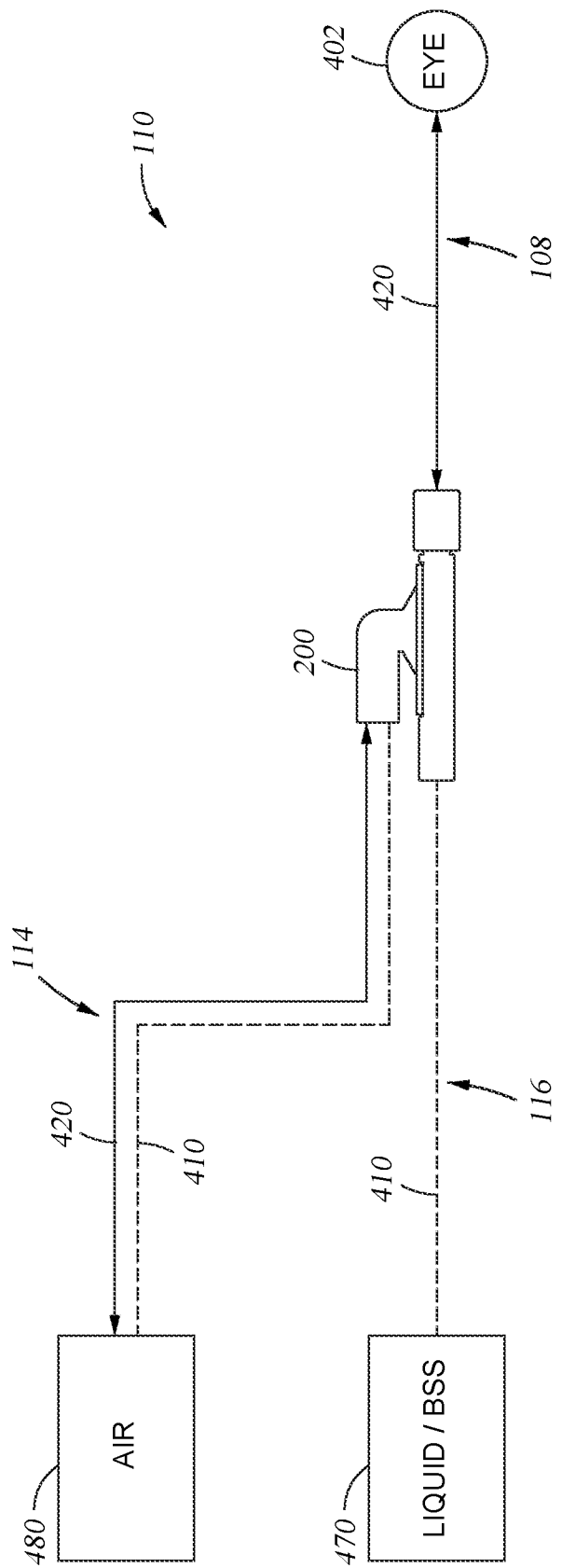
FIG. 4C illustrates a schematic plan view of an operational mode of the valve assemblies of FIGS. 2A-2C and 3A-3C, according to certain embodiments of the present disclosure.

FIGS. 4A-4C schematically illustrate operational modes of the valve assemblies 200, 300 during fluid infusion procedures. In particular, FIGS. 4A-4C illustrate the flow of liquid solutions (e.g., BSS), represented by lines 410, and the flow of gases (e.g., air), represented by lines 420, through the fluid infusion system 110 having the valve assembly 200, as described above. Please note that although the valve assembly 200 is depicted in FIGS. 4A-4C, the valve assembly 300 may be utilized in substantially the same manner. Further, please note that unbroken lines (e.g., continuous lines) represent open or active flow, while broken lines (e.g., dashed lines) represent closed or no flow.

FIG. 4A depicts the fluid infusion system 110 during a first operation of liquid infusion, which may be selected and/or controlled by a user (e.g., a surgeon) via a surgical console, such as surgical console 100. As shown, infusion liquid 410 is controllably flowed between the liquid source 470 and eye 402 via liquid supply line 116, valve assembly 200, and infusion line 108, while air or gas flow through gas supply line 114 is stopped or shut off. To control a pressure within the fluid infusion system 110 and thus, the eye 402, the user may adjust the direction and flow rate of the liquid 410 to or from the liquid source 470 via the surgical console 100. The valve assembly 200 (e.g., a flow control valve) enables liquid 410 to flow between the liquid supply line 116 and the infusion line 108, while also preventing the liquid 410 from flowing into the gas supply line 114 and towards the gas source 480 due to the presence of the hydrophobic filter 222. Accordingly, the valve assembly 200 provides a passive means of preventing leakage of liquid 410 into gas supply line 114, which contrasts with conventional flow control valves that may allow the escape of at least some liquid 410 into the gas supply line 114 during use thereof.

FIG. 4B depicts the fluid infusion system 110 during a second operation of liquid infusion in which the pressure of air 420 within the gas supply line 114 is actively modulated while infusion liquid 410 is flowed between the liquid source 470 and eye 402. As described above, the pressure within the fluid infusion system 110 and the eye 402 is controlled by adjusting the direction and flow rate of the liquid 410 to or from the liquid source 470 via the surgical console 100. When left unchecked, pressure within the gas supply line 114 may inadvertently build up during infusion and cause air 420 to leak into the liquid 410 being injected into the eye 402, thereby negatively affecting the intraocular pressure thereof. Therefore, in certain embodiments, it may be desired to apply a vacuum pressure (e.g., negative pressure) to the gas supply line 114 to vent the gas supply line 114 and prevent the undesired escape of air 420 into the liquid 410 as bubbles. In certain embodiments, active venting of the gas supply line 114 may also be desired to purge the infusion liquid 410 of gases already trapped therein as the liquid 410 passes into the infusion line 108.

Since conventional flow control valves cannot prevent the leakage of liquid 410 into the gas supply line 114, venting of the gas supply line 114 with a conventional valve is extraordinarily difficult. In comparison, as a result of the hydrophobic filter 222, the valve assembly 200 facilitates active venting of the gas supply line 114 during infusion of liquid 410 into the eye 402, thus reducing or eliminating the possibility of unwanted gases being flowed into eye 402 and disrupting the intraocular pressure therein.

FIG. 4B is further representative of the fluid infusion system 110 during an infusion fluid back-flow operation. Back-flow of infusion fluids may be necessitated when the eye 402 is injected, via a separate cannula or injection device, with a retinal tamponade (or other fluid treatment) such as intraocular air/gas, silicone oil, or perfluoron. As a result, infusion fluids previously flowed through the infusion line 108 may need to be back-flowed. Because conventional flow control valves cannot backflow or purge gases into the gas supply line 114 without leakage of infusion liquid, only a limited volume of infusion fluids can be back-flowed without risking the chance of liquid leakage into the gas supply line 114 or gas leakage into the liquid supply line 116. In contrast, the hydrophobic filter 222 of the valve assembly 200 in FIG. 4B enables backflow of gases into the gas supply line 114 without leakage of infusion liquids, thus allowing a greater volume of the infusion fluids to be back-flowed into their respective supply lines and further enabling a greater volume of treatment fluids to be injected into the eye 402.

FIG. 4C depicts the fluid infusion system 110 during a third operation of liquid infusion. The operational mode depicted in FIG. 4C may be performed, for example, during a fluid-air exchange to help push out subretinal fluid from the intraocular space of the eye 402. As shown, air 420 is flowed from the gas source 480 to the eye 402, while liquid flow through the liquid supply line 116 is shut off to prevent escape of liquid 410 into the infused air 420. Accordingly, the pressure within the fluid infusion system 110 and the eye 402 is controlled by adjusting the direction and flow rate of the air 420 to or from the gas source 480 via the surgical console 100.

In summary, embodiments of the present disclosure include structures and mechanisms for improved intraocular pressure maintenance during ophthalmic procedures, and in particular, improved fluid control valves for intraocular fluid infusion. The valve assemblies described above include embodiments wherein a hydrophobic filter is disposed between a gas supply line and a liquid supply line and/or infusion line. The utilization of the hydrophobic filter enables bi-directional flow of gases between a gas supply line and the patient's eye, while also passively preventing the leakage of liquids into the gas supply line. Accordingly, the aforementioned valve assemblies are particularly beneficial during fluid infusion of the intraocular space, as gas may be vented from infusion liquids during infusion or black-flowed from the eye during injection of other treatments, thus allowing better control of the intraocular pressure within the eye.

While the foregoing is directed to embodiments of the present disclosure, other and further embodiments of the disclosure may be devised without departing from the basic scope thereof, and the scope thereof is determined by the claims that follow.

What is claimed is:

1. A valve assembly configured for bi-directional flow of gas and infusion liquid therethrough during ophthalmic procedures, comprising:
   a first portion configured to allow a bidirectional flow of gas therethrough, comprising:
      a first conduit having a first port configured to couple to a source of gas; and
      a first cavity having a first end and a second end opposite the first end, the first end fluidly coupled to the first port via the first conduit, the second end having a cross-sectional area greater than a cross-sectional area of the first conduit;
   a second portion configured to allow bi-directional flow of gas and infusion liquid therethrough, comprising:
      a second conduit having a second port and a third port on an opposing side of the second conduit as the second port, wherein the second port, the second conduit, and the third port provide a first flow passageway through the second port, the second conduit, and the third port; and
      a second cavity in fluid communication with the second port and the third port, the second cavity adjacent to the first cavity;
      wherein the second port is configured to couple to a source of liquid and wherein the third port is configured to couple to an infusion line for an ophthalmic surgical site; and
   a filter partitioning the first cavity from the second cavity, the filter comprising a hydrophobic membrane partially defining the second cavity along a planar face of the hydrophobic membrane;
   wherein the first portion, the filter, and the second portion are configured to allow a flow of gas from the first port, through the first portion, through the filter, through the second portion, and out of the third port;
   wherein the first portion, the filter, and the second portion are further configured to allow a flow of gas from the third port, through the second portion, through the filter, through the first portion, and out the first port; and wherein the first portion, the filter, and the second portion are further configured to allow a flow of infusion liquid from the second port, through the second portion, and out the third port while further configured to provide vacuum from the first port to aspirate gas from the flow of infusion liquid in the second portion, such that the aspirated gas flows from the infusion liquid in the second portion, through the filter, through the first portion, and out the first port.

2. The valve assembly of claim 1, wherein the hydrophobic membrane is configured to prevent a flow of liquid from the second cavity into the first cavity while allowing bi-directional flow of gas therebetween.

3. The valve assembly of claim 1, wherein the hydrophobic membrane comprises at least one of polytetrafluoroethylene (PTFE), expanded PTFE (ePTFE), polycarbonate track etch (PCTE), polyester, nylon, cellulose, cellulose nitrate (CN), cellulose acetate (CA), polyethersulfone (PES), glass fiber, and acrylic copolymer.

4. The valve assembly of claim 3, wherein the filter further comprises a backing coupled to the hydrophobic membrane, the backing comprising at least one of polyester, polyethylene, polypropylene, and nylon.

5. The valve assembly of claim 1, wherein the hydrophobic membrane has a pore size in a range of 0.1 μm to 10.0 μm and a thickness in a range of 150 μm to 300 μm.

6. The valve assembly of claim 1, wherein the first cavity further comprises one or more semi-annular or annular ridges disposed therein, the one or more ridges defining one or more channels.

7. The valve assembly of claim 6, wherein the second cavity further comprises one or more semi-annular or annular ridges disposed therein, the one or more ridges defining one or more channels.

8. The valve assembly of claim 1, wherein at least a portion of the second cavity has a cross-sectional area substantially the same or greater than the cross-sectional area of the second end of the first cavity.

9. The valve assembly of claim 1, wherein a second flow passageway between the first conduit and the first cavity is perpendicular to the first flow passageway through the second port, the second conduit, and the third port.

10. The valve assembly of claim 1, wherein the third port comprises a luer lock.

11. The valve assembly of claim 1, wherein the first flow passageway between the second cavity and the second conduit has a smaller diameter than a second flow passageway between the first cavity and the first conduit.

12. The valve assembly of claim 1, wherein a second flow passageway through the first port is parallel to the first flow passageway through the second port, the second conduit, and the third port.

13. The valve assembly of claim 1, wherein the flow passageway through the second port, second conduit, and third port is straight.

14. The valve assembly of claim 13, wherein the first flow passageway through the second port, the second conduit, and the third port is parallel to the planar face of the hydrophobic membrane.

15. The valve assembly of claim 13, wherein the first flow passageway through the second portion provides unimpeded flow from the second port to the third port without an intervening filter.

* * * * *